(12) United States Patent
Baets et al.

(10) Patent No.: US 7,217,349 B2
(45) Date of Patent: May 15, 2007

(54) METHOD OF SEPARATING MULTIVALENT IONS AND LACTATE IONS FROM A FERMENTATION BROTH

(75) Inventors: Peter Baets, Gorinchem (NL); Willem Jacob Groot, Dordrecht (NL)

(73) Assignee: Purac Biochem B.V., Gorinchem (NL)

( * ) Notice: Subject to any disclaimer, the term of this patent is extended or adjusted under 35 U.S.C. 154(b) by 238 days.

(21) Appl. No.: 10/693,922

(22) Filed: Oct. 28, 2003

(65) Prior Publication Data
US 2004/0137587 A1    Jul. 15, 2004

(30) Foreign Application Priority Data
Oct. 28, 2002  (EP) .................................. 02079493

(51) Int. Cl.
*B01D 61/44*    (2006.01)
(52) U.S. Cl. ................ 204/537; 204/539; 204/540; 204/541; 204/543; 204/544
(58) Field of Classification Search ........... 204/537, 204/539, 540, 541, 543, 544, 631, 630
See application file for complete search history.

(56) References Cited

U.S. PATENT DOCUMENTS

| | | | |
|---|---|---|---|
| 5,681,728 A | 10/1997 | Miao | |
| 5,746,920 A | 5/1998 | Krischke et al. | |
| 6,221,225 B1 | 4/2001 | Mani | |
| 6,331,236 B1 | 12/2001 | Mani | |
| 6,495,013 B2 * | 12/2002 | Mazur et al. | ................ 204/525 |
| 2002/0005356 A1 | 1/2002 | Mazur et al. | |

* cited by examiner

*Primary Examiner*—Arun S. Phasge
(74) *Attorney, Agent, or Firm*—Oliff & Berridge, PLC

(57) ABSTRACT

The invention pertains to a method of separating multivalent ions and lactate ions from a fermentation broth comprising a multivalent ion lactate salt by using an electrodialysis or electrolysis apparatus, comprising the steps of introducing the broth wherein the multivalent ion concentration is at least 0.1 mole/l, the lactate ion concentration is less than 300 g/l, and less than 10 mole % of the lactate ion are other negatively charged ions, into a first compartment of the electrodialysis or electrolysis apparatus, which compartment is limited by an anion-selective or non-selective membrane and a cathode, and wherein the multivalent ion is converted to obtain a residual stream comprising the hydroxide of the multivalent ion, and the lactate ion is transported through the anion-selective or non-selective membrane into a second compartment limited by the anion-selective or non-selective membrane and an anode, after which the lactate ion is neutralized to lactic acid.

11 Claims, 2 Drawing Sheets

METHOD OF SEPARATING MULTIVALENT IONS AND LACTATE IONS FROM A FERMENTATION BROTH

The invention pertains to a method of separating multivalent ions and lactate ions from a fermentation broth comprising a multivalent ion lactate salt by using an electrodialysis or electrolysis apparatus. The invention further relates to an electrodialysis or electrolysis apparatus for separating a fermentation broth into a residual stream comprising multivalent ions and lactate ions.

Methods of separating monovalent ions and lactate ions from a fermentation broth comprising a monovalent ion lactate salt by using an electrodialysis or electrolysis apparatus are well known in the art. In U.S. Pat. No. 5,002,881 a process is described for the fermentative preparation of lactic acid by fermenting a culture of Bacillus in an aqueous solution comprising sodium, potassium or ammonium ions, subjecting the reaction mixture to ultrafiltration and subjecting the permeate to an electrodialysis wherein bipolar membranes are used.

Preferred lactic salts are sodium, potassium, and ammonium lactates, as was also disclosed in U.S. Pat. No. 5,681,728, which further makes use of an electrodialysis apparatus to purify sodium, potassium, or ammonium lactate from a complex feed stream.

Exclusively sodium, potassium, or ammonium salts of lactic acid are used, because these are water-soluble and it is important to prevent fouling of the membrane and the electrodes. It is generally thought that fouling by multivalent ions would frustrate the electrodialysis process, and necessitates regular cleaning of the equipment and therefore interrupting the process. For economical reasons this is an unwanted situation. Therefore, it is commonly accepted that multivalent ions should be prevented in the electrodialysis process.

However, the neutralization in the fermentation process is preferably performed with multivalent ions, not with sodium, potassium, or ammonium hydroxide. In WO 9828433 a method is proposed to prevent scaling on purifying divalent salts of lactic acid, as obtained after the fermentation process. The permeate of an ultrafiltration process, for that reason, is treated in an ion exchange unit to bind calcium and magnesium ions, and other multivalent ions like iron ions, if present. This method prevents the precipitation of salts, such as calcium phosphate that may lead to irreversible scaling of the membrane. However, this method requires an extra exchange step and thereby makes the end product more expensive.

Specific electrodialysis processes and apparatus for converting sodium and ammonium lactate tot lactic acid anion have been described in U.S. Pat. No. 6,221,225 and U.S. Pat. No. 6,331,236. In these patents a stack of electrodialysis cells is used to form a multiplicity of compartments for separation. In both patents methods are described to remove multivalent ions in order to prevent fouling in the electrodialysis process. Exclusively monovalent ions are treated in the electrodialysis processes of above-mentioned patents. An example is given of an electrodialysis process for the monovalent ammonium salt of lactic acid. The methods of both patents require additional equipment and chemicals, which make the processes for electrodialysis complicated and expensive. In U.S. Pat. No. 6,221,225 multivalent ions are removed by ion exchange or nanofiltration prior to the electrodialysis process. In U.S. Pat. No. 6,331,236 chelating agents are used in the electrodialysis cell to bind or chelate with the multivalent ions to form metal-chelate buffers. An ion exchange membrane within the electrodialysis cell separates these metal-chelate buffers from the monovalent ions to be treated further in the electrodialysis cell.

In U.S. Pat. No. 5,746,920 a pre-purification step is used prior to the electrodialysis process. An example is given of cell-free fermentation broth containing sodium lactate that is passed through a bipolar electrodialysis to yield lactic acid. The electrodialysis step can only handle monovalent ions as sodium lactate, since multivalent ions would lead to fouling as mentioned earlier. The broth is therefore submitted to a pre-purification step before entering the electrodialysis cell in order to remove multivalent cations from the feed to the electrodialysis cell.

Many processes for electrodialyses use cation-selective membranes within the cell for separation of the monovalent cations from the feed stream to the electrodialysis cell. Transport of multivalent cations through these membranes however introduces a very high risk of fouling.

Sometimes bipolar membranes are used in combination with one or more cation-selective membranes. The bipolar membranes are used to split the water into hydroxides and protons. The hydroxides form complexes with the cations and the protons are used to form free acid with the remaining anions of the feed stream. An additional anion-selective membrane may be used to further separate the anions from the feed stream. In general, cation-selective membranes and bipolar membranes are more expensive than anion-selective membranes. In patent applications US 2002/0005356, U.S. Pat. No. 6,495,013 and WO02/05933 a process and apparatus is described that use a combination of cation-selective membranes with bipolar membranes with optionally an anion selective membrane included for electrodialysis of multivalent ions. The introduction of an acid forms the solution for overcoming the problem of fouling by the multivalent ions. The acid is introduced in compartments of the cell and neutralizes formed solids. Introduction of additional chemicals of course also leads to increased costs.

It is therefore an objective of the present invention to provide a method of directly separating multivalent ions and lactate ions from a fermentation broth comprising a multivalent ion lactate salt by using an electrodialysis or electrolysis apparatus, without the need of an extra step for removal of multivalent ions or the introduction of additional chemicals for preventing fouling by the precipitation of complexes formed by multivalent ions.

The present invention provides in a method satisfying the above conditions by performing the method comprising the steps of introducing the broth wherein the multivalent ion concentration is at least 0.1 mole/l, the lactate ion concentration is less than 300 g/l, and less than 10 mole % of the lactate ion are other negatively charged ions, into a first compartment of the electrodialysis or electrolysis apparatus, which compartment is limited by an anion-selective or non-selective membrane and a cathode, and wherein the multivalent ion is converted to obtain a residual stream comprising the hydroxide of the multivalent ion, and the lactate ion is transported through the anion-selective or non-selective membrane into a second compartment limited by the anion-selective or non-selective membrane and an anode, after which the lactate ion is neutralized to lactic acid.

After isolation of the lactic acid, the lactic acid may be further purified by purification steps known in the field such as distillation, extraction, filtration, adsorption, ion exchange and the like, concentration, evaporation and carbon treatment.

The method according to the invention preferably makes use of a broth containing per equivalent of lactate ion at least 0.1 equivalent of the multivalent ion, and more preferably at least 0.3 equivalents of the multivalent ion. Preferably, the multivalent ion concentration in the broth is 0.1–1.5 mole/l. The broth is obtained by the common procedure such as by fermentation of a carbohydrate (for instance glucose, starch, sucrose, and the like).

The multivalent ion is preferably a multivalent metal ion selected from magnesium, calcium, zinc, iron, and aluminum, and mixtures thereof.

In another preferred embodiment according to the invention the fermentation broth comprises microorganisms. It has advantages to recycle the residual stream to the fermentation broth. It also has advantages when the hydroxide of the multivalent ion is at least partially present as solid in slurry. Further, it has advantages with respect to prevention of fouling by precipitation of complexes formed by the hydroxides with multivalent cations to recycle lactic acid from any step later in the purification process to the electrodialysis or electrolysis process.

In a particularly preferred embodiment according to the invention the membrane through which the lactate ions are transported is an anion-selective membrane.

By transporting the lactate ions through membranes instead of the cations, the lactate is isolated from the remaining feed stream and impurities. Next to this purification step, an anion-selective membrane prevents transport of possibly precipitating cations in the membranes.

In the electrodialysis or electrolysis process according to the invention, the process uses in the first compartment a second membrane being an anion-selective membrane, a non-selective membrane, or a bipolar membrane having its cation-selective side directed to the cathode.

In another embodiment according to the invention the electrodialysis or electrolysis process uses in the first compartment alternating anion-selective or non-selective membranes, and bipolar membranes having their cation-selective sides directed to the cathode. Most preferred these extra membranes are of the anion-selective type.

The invention further relates to an apparatus for performing the above-mentioned methods. Thus according to the invention there is provided an electrodialysis or electrolysis apparatus for separating a fermentation broth into a residual stream comprising multivalent ions and lactate ions, comprising a first compartment which is limited by an anion-selective or non-selective membrane, preferably an anion-selective membrane, and a cathode, which further comprises means for introducing the fermentation broth, and a second compartment limited by the anion-selective or non-selective membrane and an anode, which further comprises means for removing lactic acid, and optionally means for recycling lactic acid to the first compartment from any step later in the purification process and optionally means to recycle the residual stream of the first compartment to the fermentation broth.

The above-mentioned electrodialysis or electrolysis apparatus may contain a first compartment further comprising a second membrane being an anion-selective membrane, a non-selective membrane, or a bipolar membrane having its cation-selective side directed to the cathode.

In another embodiment according to the invention the electrodialysis or electrolysis apparatus comprises a first compartment with alternating anion-selective or non-selective membranes, and bipolar membranes having their cation-selective sides directed to the cathode. Most preferred these extra membranes are of the anion-selective type.

The invention is illustrated by the following figures.

FIG. 1 is a schematic view of an electrodialysis or electrolysis apparatus in its simplest form, i.e. containing an anode and a cathode and an anion-selective or non-selective membrane in between.

Figure 1:
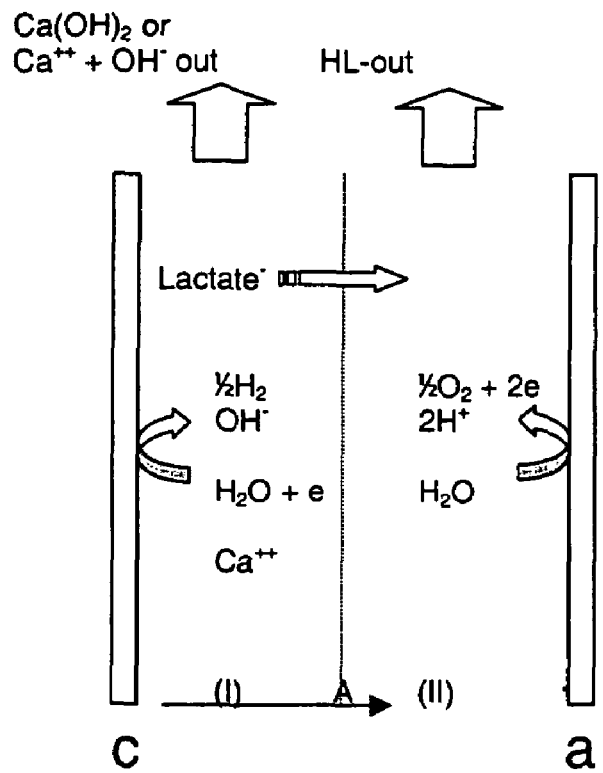

In FIG. 1 an electrodialysis or electrolysis cell is shown with an anode (a) indicated with charge+ and a cathode (c) indicated with charge −. Between the anode and cathode a membrane (A) is placed which can be an anion-selective or non-selective membrane. Examples of anion-selective and non-selective membranes can be found in literature handbooks (eg. K. Scott, Handbook of industrial membranes, $2^{nd}$ edition, 1998, ISBN 1856172333, p. 257–269; Perry's Chemical Engineers' Handbook, sixth edition, R. H. Perry, D. Green, 17–14/17–34 and 17–36/17–45; and Kirk-Othmers Encyclopedia of Chemical Technology, Third Edition, Vol. 8, p. 698, Chapter Diaphragms). These membranes may be available in various physical forms including mats, sheets, films, sintered forms, and woven or non-woven cloths.

Thus the cell comprises a first compartment (I), which compartment is limited by the anion-selective or non-selective membrane (A) and the cathode (c). In this example calcium lactate is placed in compartment (I), after which on applying current in the cell the calcium ions form calcium hydroxide that may at least partially deposit in compartment (I) and leaves this compartment either as a solution of ions or as a solid hydroxide-containing slurry, whereas the lactate anion passes through the membrane (A) and leaves the second compartment (II), which compartment is limited by the anion-selective or non-selective membrane (A) and the anode (a), as lactic acid (HL). The figure further shows the electrolytic reactions that occur, wherein hydrogen is formed at the cathode and oxygen at the anode.

Figure 2:
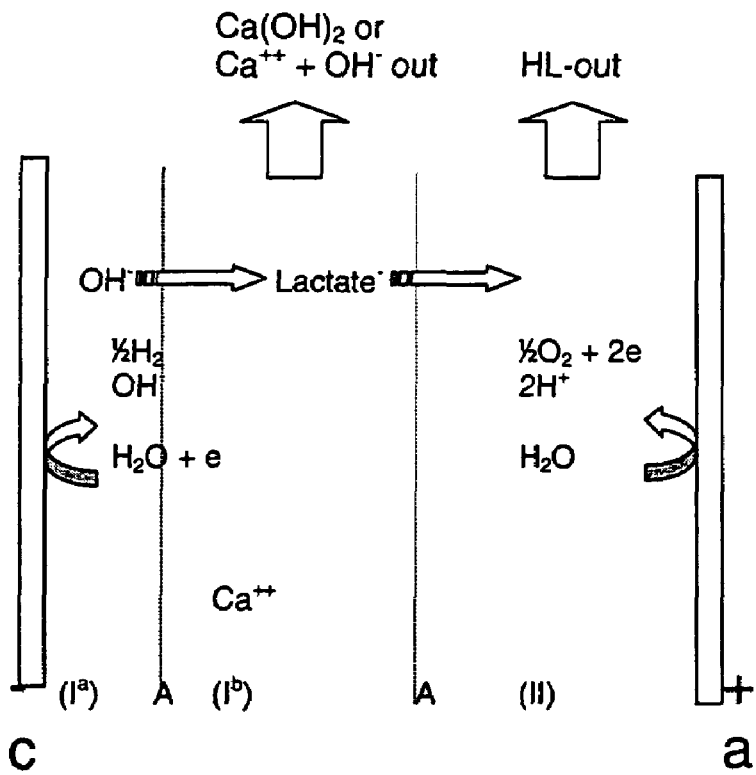
FIG. 2 is a schematic view of an electrodialysis or electrolysis apparatus comprising a second anion-selective membrane.

In FIG. 2 an embodiment is shown according to claim 13, wherein the first compartment further comprises a second anion-selective or non-selective membrane or bipolar membrane (A), dividing compartment (I) in two parts, i.e. $I^a$ and $I^b$. The electrolysis processes occurring in this cell are the same as shown in FIG. 1, but the additional anion-selective, non-selective membrane or bipolar membrane acts as an extra protecting membrane, further preventing fouling of the multivalent ion at the cathode and/or anode. According to this embodiment the multivalent salt (in this particular case calcium) of lactic acid is introduced in section $I^b$ of compartment I, keeping the calcium physically away from both the anode and cathode.

Figure 3:
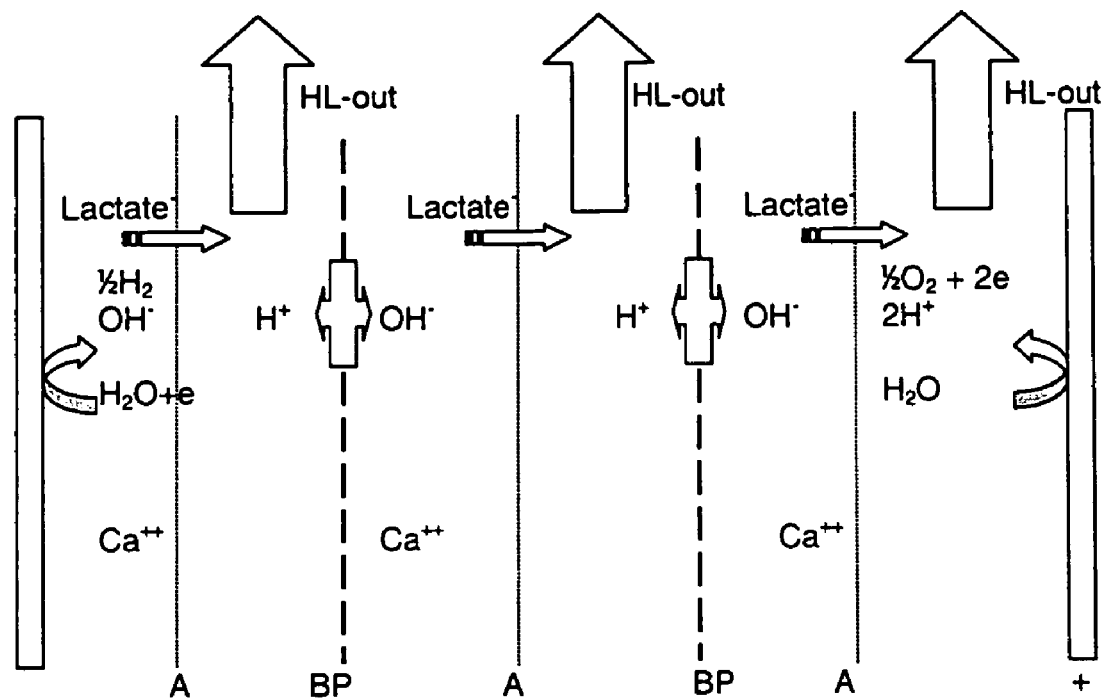
FIG. 3 is a schematic view of an electrodialysis or electrolysis apparatus with alternating anion-selective and bipolar membranes.

In FIG. 3 an embodiment is shown according to claim 11, wherein a stack of three cell combinations has been formed. According to this embodiment, anion-selective or non-selective membranes (A), preferably anion-selective membranes, alternate with bipolar membranes (BP) having their cation-selective sides directed to the cathode. The compartments indicated with $Ca^{++}$ are compartments wherein the multivalent salt of lactic acid is introduced. The electrodialysis process is in principle the same as that of FIGS. 1 and 2, but lactic acid (HL) leaves the cell in three different product streams. It is clear that according to this principle any stack with any number of cells can be made, which will improve efficiency of membranes and power input and decrease costs.

The invention is further illustrated with the following non-limitative examples.

In following examples lactic acid concentrations have been measured by titration with a sodium hydroxide solution of 1.0033 M.

EXAMPLE 1

A cell according to FIG. 1 comprises an ACM™ membrane (ex Tokuyama), a titanium cathode and a DSA anode, the distance of the cathode and anode to the membrane being both 8 mm. The membrane surface is 10*10 cm$^2$ and the volume of each of the compartments is 80 cm$^3$. The current is adjusted to 40 mA/cm$^2$ (4 A). The liquid yield is 117 l/h at the anolyte and 105 l/h at the catholyte at a working temperature of 55° C. The catholyte volume is 2 l, comprising a 12 wt. % calcium lactate solution, and the anolyte volume is 0.5 l, comprising a 5 wt. % lactic acid solution initially. The pH of the catholyte during the experiment is kept below 10 by addition of acid (90 ww % lactic acid).

The voltage could be kept between 15 and 19 V to maintain a current of 4 A during this experiment (5 h), during which time the concentration of lactic acid increases from 5 wt. % to 17.4 wt. %. The electrodes remained free from scaling as was observed visually.

EXAMPLE 2

The experiment of Example 1 was repeated, keeping the conditions the same with the exception that the liquid yield is 114 l/h at the anolyte and 120 l/h at the catholyte at a working temperature of 60° C.

Contrary to Example 1 no acid was added during the experiment. The voltage was kept between 13.9 and 18.6 V to maintain a current of 4 A during this experiment (122 min), during which time the pH increased to 12.43. The catholyte became white, due to the formation of a calcium hydroxide slurry, but the electrodes remained free from scaling. Again, this was noticed by visual observation. The lactic acid concentration increased from 5 ww % to 10 ww % during the experiment.

EXAMPLE 3

Figure 4:
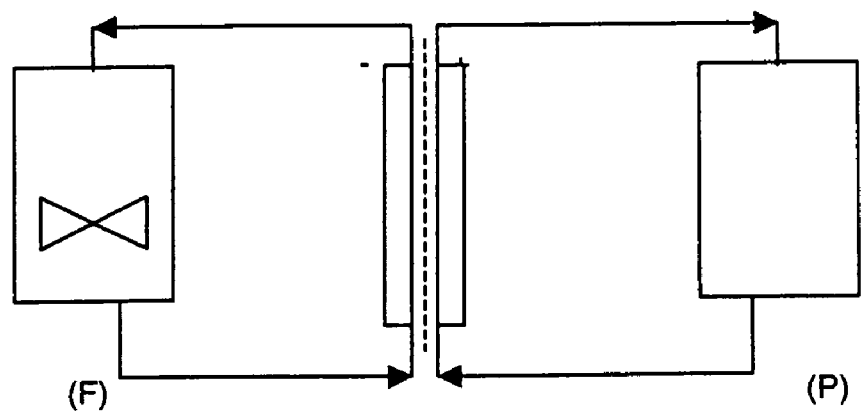
FIG. 4 is a scheme showing the electrodialysis or electrolysis apparatus according to FIG. 1, a product container (P), and the fermentor (F) for converting the carbohydrates (e.g. sugar) to a multivalent salt of lactic acid.

An electrolysis cell according to FIG. 1, using a non-selective porous cellulose acetate membrane (pore diameter 0.8 μm; ex Sartorius), was used in combination with a feed container, and a fermentor for converting the feed to a multivalent salt of lactic acid, as depicted in FIG. 4. The fermentation of sucrose to lactic acid was started by addition of a calcium hydroxide slurry to control the pH at 6.4 and after 20 h, which time is necessary to obtain a sufficient amount of conductive salt, the addition of the above-mentioned calcium hydroxide slurry was stopped and the electrolysis was started under pH control. The pH of the fermentation was kept at 6.4. The lactate anion was transported from fermentor (F) to feed container (P) (see FIG. 4) through the membrane by applying current. The pH in P (the 12 wt. % calcium lactate solution at 54° C.) decreased during this process (see Table), showing that lactic acid was separated from the fermentation liquid.

Table

| Time (min) | pH (calcium lactate) | I (A) | V |
|---|---|---|---|
| 0 | 5.61 | 0.5 | 2.35 |
| 90 | 4.86 | 0.67 | 2.82 |
| 180 | 4.55 | 0.78 | 2.99 |
| 260 | 4.40 | 0.67 | 2.89 |
| 310 | 4.34 | 0.72 | 2.96 |

The invention claimed is:

1. A method of separating multivalent ions and lactate ions from a fermentation broth comprising a multivalent ion lactate salt by using an electrodialysis or electrolysis apparatus, the method comprising:
   introducing the broth into a first compartment,
   said broth having a multivalent ion concentration of at least 0.1 mole/l,
   said broth having a lactate ion concentration of less than 300 g/l,
   said broth including negatively charged ion that is not lactate ion in an amount of less than 10 mole % based on a total amount of lactate ion in said broth, and
   said first compartment being limited by an anion-selective or non-selective membrane and a cathode;
   converting the multivalent ion to obtain a residual stream comprising a hydroxide of the multivalent ion;
   transporting the lactate ion through the anion-selective or non-selective membrane into a second compartment,
   said second compartment being limited by the anion-selective or non-selective membrane and an anode; and
   neutralizing the lactate ion to lactic acid;
   wherein the multivalent ion is a multivalent metal ion selected from the group consisting of magnesium, calcium, zinc, iron, aluminum, and mixtures thereof.

2. The method according to claim 1 wherein the broth contains per equivalent of lactate ion at least 0.1 equivalent of the multivalent ion.

3. The method according to claim 1 wherein the multivalent ion concentration in the broth is 0.1–1.5 mole/l.

4. The method according to claim 1 wherein the fermentation broth comprises microorganisms.

5. The method according to claim 1 wherein the residual stream is recycled to the fermentation broth.

6. The method according to claim 5 wherein the hydroxide of the multivalent ion is at least partially present as solid in slurry.

7. The method according to claim 1 wherein the lactic acid is recycled to the first compartment.

8. The method according to claim 1 wherein the anion-selective or non-selective membrane is an anion-selective membrane.

9. The method according to claim 1 wherein a second membrane is used within the first compartment being an anion-selective membrane, a non-selective membrane, or a bipolar membrane having its cation-selective side directed to the cathode.

10. The method according to claim 1 wherein within the first compartment alternating anion-selective or non-selective membranes and bipolar membranes are used having their cation-selective sides directed to the cathode.

11. The method according to claim 1, wherein the broth contains per equivalent of lactate ion at least 0.3 equivalents of the multivalent ion.

* * * * *